United States Patent
Shimosawa et al.

[11] Patent Number: 5,968,424
[45] Date of Patent: Oct. 19, 1999

[54] MANUFACTURING METHOD FOR ARTIFICIAL TOOTH

[75] Inventors: Shigeru Shimosawa, Nara; Takashi Nokubi, Osaka, both of Japan

[73] Assignee: Shigeru Shimosawa, Japan

[21] Appl. No.: 09/073,037

[22] Filed: May 5, 1998

[30] Foreign Application Priority Data

May 7, 1997 [JP] Japan .................................. 9-134406
Mar. 24, 1998 [JP] Japan .................................. 10-096764

[51] Int. Cl.⁶ .................................................. A61C 13/083
[52] U.S. Cl. ............................... 264/19; 264/20; 264/28; 264/603
[58] Field of Search .................... 264/19, 20, 28, 264/603

[56] References Cited

U.S. PATENT DOCUMENTS

| | | | |
|---|---|---|---|
| 2,196,258 | 4/1940 | Erdle | 264/20 |
| 2,337,036 | 12/1943 | Erdle | 264/20 |
| 2,765,512 | 10/1956 | Nesbit | 264/28 |
| 2,869,215 | 1/1959 | Smith | 264/28 |
| 4,931,241 | 6/1990 | Freitag | 264/86 |
| 5,156,856 | 10/1992 | Iwasaki | 264/86 |

*Primary Examiner*—James Derrington
*Attorney, Agent, or Firm*—Thompson Hine & Flory LLP

[57] ABSTRACT

A ceramic powder having a uniform particle diameter of 50 $\mu$m or smaller is used as a dental ceramic powder to produce a high-precision and compact artificial tooth. The ceramic powder fired assures a non-porous and compact structure of the artificial tooth. In a manufacturing method for the artificial tooth, the cream of ceramic powder is poured into a core, the core with the ceramic cream loaded is frozen to shape, thawed, dried and then fired in a furnace. To assure even more compact structure, the cream is compacted and hardened prior to freezing. Pressure is efficiently applied in the compaction and hardening process.

15 Claims, 1 Drawing Sheet

[Fig. 1]
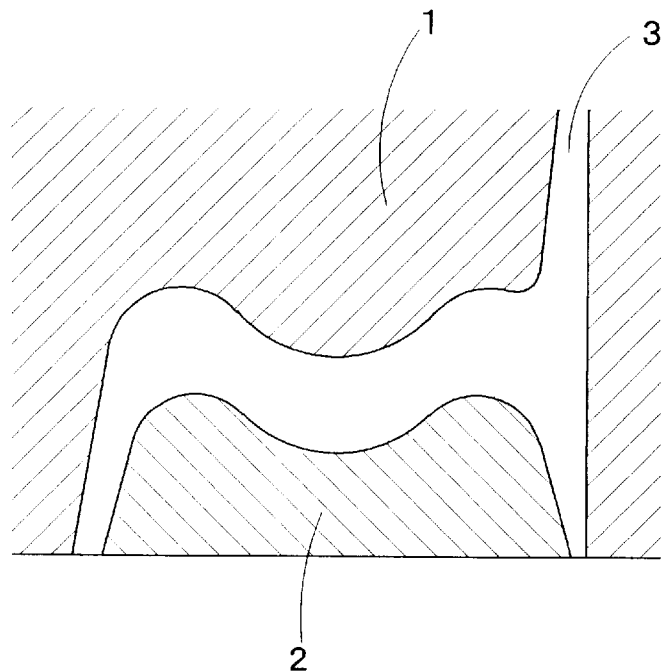
[Fig. 2]
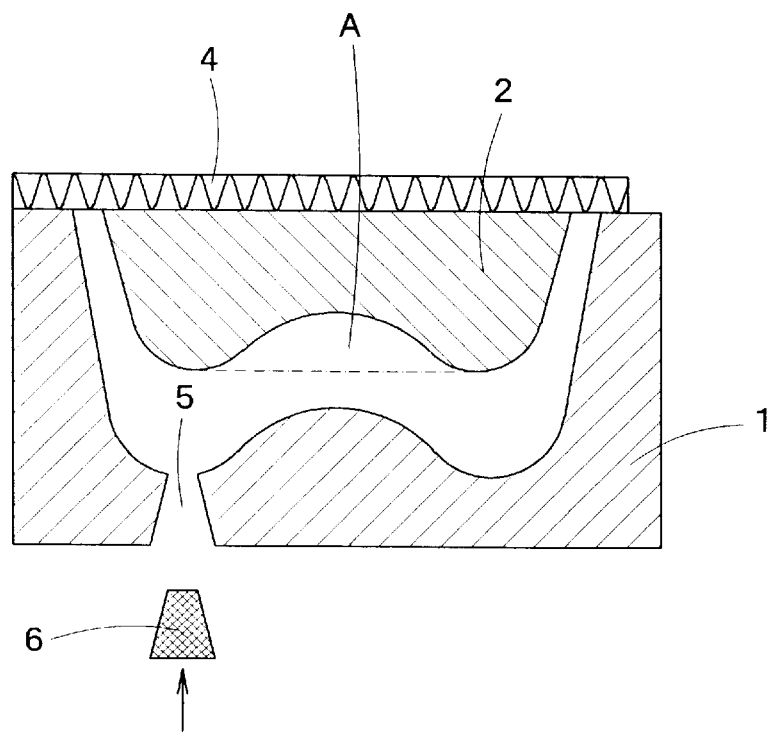

MANUFACTURING METHOD FOR ARTIFICIAL TOOTH

BACKGROUND OF THE INVENTION

1. Field of the Invention

The present invention relates to ceramic powder that forms a fine ceramic product which is used to produce an artificial tooth at a dental laboratory and also relates to a method of producing an artificial tooth by settling a ceramic product.

2. Description of the Related Art

Ceramic powders are chiefly used to restore the crown of a tooth or to form an artificial tooth in dental clinics today. In one method, a ceramic powder is dissolved in water or a special mixture liquid mixed with an additive such as glycerin that slows drying for assuring an easy-to-handle feature to make a ceramic paste, which is thickened and shaped by a brush or other instruments. To match complex coloration of a tooth, ceramic powders of a plurality of colors are sequentially applied and are compacted and then hardened by adding vibration while an adjustment is gradually performed.

A high skill level is needed for a series of steps in which the ceramic powder is molded into the shape of a tooth while moisture is oozed out therefrom through vibration to compact and harden the ceramic material. Since the ceramic material needs to be free from deformation and maintain its form, ceramic powders in a wide range of particle size are mixed. When mixed, molding and vibration of the ceramic material and moisture oozing are insufficient in a mixture of ceramic powders in a wide range of particle size, particles in particular range are distributed in a localized region, leading to a localized defect after a firing process. If the localized distribution is left for a long period of time, mixture is different from position to position, and it is impossible to restore uniform distribution of the particles. Once mixed, the ceramic powders, even unused, have to be discarded at the moment drying starts.

The above-described conventional ceramic powder can be mixed in a mixing liquid such as water and then poured into a core. Since consideration is given to preventing a run of material in the course of molding in the conventional ceramic material, the pouring method does not work in the conventional ceramic powder. More specifically, when the ceramic powder is mixed in water, particles precipitate for a short period of time and are hardened inconsistently. Pouring the particles into a fine area is difficult. After pouring, the particles are distributed in a localized region, and uniformly compacting the particles through vibration is difficult. The ceramic material is thus subject to cracks and deformation in the course of drying. Especially when additional molding is performed, a crack is likely to take place during a firing process.

SUMMARY OF THE INVENTION

It is an object of the present invention to resolve the above problem in connection with an artificial tooth and its ceramic material and to provide a ceramic powder for producing a precision tooth and a manufacturing method of artificial tooth based on ceramic material settling technique using the ceramic powder.

To achieve the above object, the present invention employs a ceramic powder having a uniform particle diameter of 50 $\mu$m or smaller. In a settling technique of the ceramic material according to the present invention, a cream of ceramic powder having a uniform particle diameter is poured into a flexible core, the core and the ceramic cream are frozen, the frozen ceramic material is released from the core subsequent to the freezing, and is thawed and dried and then fired in a furnace. To assure precision in the product, the poured cream of ceramic powder is compacted and hardened through vibration to remove oozed water, and is then subjected to freezing. In this method, the ceramic powder of uniform particle diameter of 50 $\mu$m or smaller is preferably used for an effective compaction and hardening of the ceramic material and maintenance of the shape of the molded product. If the ceramic powder having a uniform particle diameter of 50 $\mu$m or smaller is used, a ceramic cream of a high flowability is provided with a small quantity of mixing liquid.

By employing the method in which the cream of ceramic powder is frozen, solidified, thawed, and dried, and then fired, a core is constructed of a soft material at the moment the cream of ceramic powder is shaped in a final form, and thereafter the formation of the ceramic material is performed in the core. The cream of ceramic powder is compacted more if a vibration is given prior to freezing and oozed water is removed. The residual water, which is frozen, then works as a release agent, facilitating the removal of the ceramic material out of the core. The margin of the ceramic material is accurately parted and an extremely high-precision artificial tooth is thus produced.

When a ceramic powder having a uniform particle diameter of 50 $\mu$m or smaller is used, the ceramic powder is mixed into a cream. The mixed cream of ceramic powder, even if dried, is reshaped by applying water. The pouring operation is thus simplified. Even when the cream of ceramic powder is compacted and hardened subsequent to the pouring into the core, the shape of the molded product is maintained with its surface kept wet. Although the chief composition of the mixing liquid is water, ethanol may be incorporated into water to prevent cracks from taking place in an additional fire step. As in the conventional art, incorporating glycerin is also possible. However, it is the experience of the inventors of this invention that an artificial tooth is colored in gray by the addition of glycerin. If the coloration is of a concern, the use of glycerin needs careful attention.

To modify the shape of an artificial tooth, the cream of ceramic powder having a uniform particle diameter of 50 $\mu$m or smaller is mixed in water to be a cream, the cream of ceramic powder is gradually molded into the shape of the artificial tooth and is then frozen, and then thawed and dried, and fired. This process permits a compaction and hardening, and preventing warps and cracks from taking place in the margin of the ceramic product during a firing process.

Preferably, the material of the core used in this invention has a high precision property and a surface smoothness that helps the core part easily from the ceramic material subsequent to freezing, permits the cream of ceramic powder to flow smoothly thereon, permits no impurities to be mixed with the cream of ceramic powder, releases easily the frozen ceramic material from the core, and has a strength so as to withstand repeated uses. Preferably, the material of the core presents an easy-to-handle feature, and is quick to cure and low cost. For this reason, an impression material of silicone rubber is appropriate for the material of core. When a high pressure is applied on the core, silicon rubber only is subject to deformation due to its insufficient hardness. In such a case, an additive such as alumina may be mixed or a rigid reinforcement may be used. The core is firmly secured so that its positional relationship with a widely used support such as a cast, a metal frame or base core remains unchanged. When such a core is used, assuring how accurate a ceramic block is kept to the core is very important to produce an artificial tooth using the freezing technique.

In view of the above, according to the present invention, the cream of ceramic powder is poured into the core for an artificial tooth, a pressure is applied to the cream of ceramic powder to compact and harden it, water oozed out under the pressure is removed, the core and the ceramic-powder cream are together frozen, and the ceramic material is then released from the core after the freezing. Of primary concern in connection with the ceramic material for forming an artificial tooth is how quickly a high density ceramic block is obtained. The inventors of this invention employ the freezing technique, which serves the purpose of carrying out the shaping for a short period of time. However, the high density and uniformity requirements have to be satisfied by different means other than the freezing technique. According to the present invention, by performing a pressurizing process prior to the freezing process, excess water is removed, the ceramic material is sufficiently compacted, and as a result, an artificial tooth becomes smooth on its surface and compact in its internal structure subsequent to the firing. If a cycle of compacting, hardening, and moisture removal is repeated for several times, an even more compact structure will result. A high-precision artificial tooth is thus provided.

The present invention provides another method. The ceramic-powder cream is poured into the core for an artificial tooth, a pressure is applied to the ceramic-powder cream to compact and harden it, additional ceramic powder is applied to water oozed out under the pressure, the core and the ceramic-powder cream are together frozen, and the ceramic material is then released from the core after freezing. In this method, oozed water is consumed for the additional ceramic powder rather than is simply discarded. The ceramic-powder cream generally shrinks its volume in the compaction and hardening process. The structure of the ceramic material is compacted under sufficient pressure while the volume of the ceramic material is gradually reduced. Since the ceramic material also shrinks in the firing process, additional ceramic powder needs to be applied subsequent to the firing process. In this method, adding ceramic material after pressurization allows the molded ceramic material to keep its compactness and volume accurate to the core. The ceramic material keeps a relatively large volume even after shrinkage, reducing additional plastering of the cream. By repeating pressurization for a plural number of times, a compact ceramic block is obtained while keeping its volume.

BRIEF DESCRIPTION OF THE DRAWINGS

FIG. 1 is a diagram showing the process of pouring the cream of ceramic powder into a core according to the present invention; and FIG. 2 is a diagram of another example of the process according to the present invention.

DESCRIPTION OF THE PREFERRED EMBODIMENTS

A preferred embodiment of the present invention is now discussed. A novel ceramic material is discussed first. A cast is shaped using a known waxing method, a metal frame is manufactured and a flexible silicone rubber core is then produced. In this embodiment, to verify the easy-to-handle feature in a uniform particle diameter, alumina ($Al_2O_3$) is used instead of a typical ceramic powder. Neither alumina nor a typical ceramic powder for dental application suffers change of properties even if water is simply added, and the results from both materials are considered identical. Each of alumina powders having diameters of about 25 $\mu$m and about 50 $\mu$m was mixed in water, and each of them became a cream. The creams were poured into silicone cores and compacted and hardened by applying vibration. Water oozed out from the alumina blocks and was removed. The alumina blocks were fully frozen at a temperature of $-25°$ C. In a freezer. The frozen alumina blocks were pulled out of the cores, and the blocks on their margin copied the fine features of the cast and were successfully released. It is considered that the water oozed out in the compaction and hardening process was frozen and then functioned as a release agent. In this embodiment, vibration was used to compact and harden the creams of alumina powders. Depending on the shape and depth of the core, the ceramic material may be destroyed rather than compacted and hardened, and the technique of applying a vibration is not a requirement in the present invention.

The ceramic materials released out of the cores were then thawed at a temperature (about 40–60° C.) slightly higher than the normal atmospheric temperature, and were dried, and then were fired at a typical temperature in a furnace. A small ceramic block suffered no large deformation keeping its form and was fit for use. A large block such as an artificial denture for the entire jaw having the dental arch is subject to deformation and the dental arch may be destroyed. Consideration needs to be given to the mounting state of the block in the furnace. A curved metal bar may be embedded in the ceramic material along the arch to control deformation. Typically, a metal frame formed through a casting process is used as a support core and the ceramic material may be wrapped around the support core. This arrangement preferably reinforces the entire structure of the ceramic block.

In the above embodiment, alumina powder was used. Dental ceramic materials are very similar to alumina powder in material property, but are not so square as alumina powder. The results of the dental ceramic material of this invention are therefore expected even better than those of the alumina powder.

More particularly, a ceramic powder having a uniform diameter of 50 $\mu$m or smaller results a high-accuracy artificial tooth like in the above embodiment.

A high-accuracy artificial tooth was thus fired by using the above-described novel technique. When a ceramic powder having a diameter of 50 $\mu$m or smaller is used, the cream of ceramic powder is obtained by mixture in water. Compaction and hardening are easy and deformation during the firing process is controlled. This technique is used during the pouring of the cream into the core, molding process and even after the molding process. A settling technique using the cream pouring into the core is now briefly discussed. In case of a large dental prosthesis for an artificial tooth or a ceramic block, the center is formed by pouring the cream first, and is then fired. After firing, the block is shrunk by about 20%. Although the degree of shrinkage of the ceramic material remains unchanged from the conventional one, a shrunk state is predictable subsequent to firing if the density of the ceramic material is constant. In this case, additional molding is possible for reshaping. In this way, the settling method finds a wide application.

A next embodiment employs pressurization for compacting and hardening the cream of ceramic powder poured into the core. A step for pouring the cream of ceramic powder into the core is first discussed. A single-color cream may be poured or multi-color creams may be poured in lamination. In either case, the ceramic material needs to be mixed in a mixing liquid and sufficiently be eliminated foams. As already described, the ceramic material is preferably uniform in diameter, but the conventional ceramic powder is also acceptable. Silicone rubber impression material was used as the material of the core. The impression material was soft and easy to release and was free from deformation. The cream was first injected through an opening of the core. With the cream poured in, the core was subjected to a next step of pressurization. A preprocess of compaction and hardening may be optionally performed by applying vibration prior to the pressurization process. The application of vibration may be omitted depending on the shape of the core.

The following two methods are available in the pressurization process. In one method, the core is accommodated in a pressure vessel to apply uniform pressure from all directions, and in the other method, pressure is applied through an opening of the core (an injection port of the ceramic material) from one direction. Which method to use is determined depending on the shape of the impression of the core and the size of the injection port. In the first method, for the nature of the ceramic cream, the injection port needs to be relatively large. Vents are provided in the core where insufficient injection of the cream takes place, where air collects in the cream, or where water oozed out in the compaction and hardening process under pressurization is not drained. The vent is properly sized such that the core may not be broken when the ceramic material is released out of the core subsequent to the freezing. When the injection port is small with the core generally closed or the thickness of the cast is thick, pressure is uniformly applied. When the core has a large exposed area, or the cast is complex with partly thin portions, the application of uniform pressure is difficult. In view of this limitation, the range of artificial tooth produced by the pressure application using the pressure vessel are also subject to a limitation. Since the pressure by the pressure vessel is not so high (up to 7 kg/cm$^2$), no particular conditions are set about the core structure and the injection of the ceramic cream, and the process using the pressure vessel is thus easy. In this embodiment, a single pressurization is used. When a plurality of ways of pressurization are performed, the above step is simply repeated to required number of times.

Applying a pressure strong enough to compact and harden the ceramic material, the press performs precise compaction. The press linearly compacts the ceramic material, and the core is partitioned into parts in the direction of pressure. After pouring the ceramic cream into a lower core, an upper core is placed on the lower core and the press is used to compact the ceramic cream. Although the compaction pressure depends on the ability of the press, a very high pressure may be applied. Under pressure, excess water and excess cream are naturally forced out. Applying vibration, while compacting with the press, works. When the press applies pressure, the core itself needs to withstand the pressure. An appropriate material needs to be selected to produce a robust core. When the core is rearranged for pressurization in case the cream fails to flow smoothly, the core is difficult to fit to its original position; therefore, a high-precision core needs to be produced. Like the pressure vessel, if pressure is applied in a plural number of times, each application is performed subsequent to the addition of ceramic cream.

Available for the removal of water is the method of using a water absorption pad which absorbs water oozed out of the surface of the ceramic material under pressure. The present invention is not limited to this. It is important to separate, from the ceramic block, excess water oozed out under pressure. As long as it serves this purpose, any method for the removal of water falls within the present invention. In this embodiment, excess water is removed. Alternatively, additional ceramic powder may be fed. In this case, ceramic powder matching the quantity of oozed water is added and lightly mixed, and then the ceramic block is again put under pressure. Conditions of the core, injection conditions and pressurization conditions remain unchanged from those for the removal of water.

The ceramic block, compacted and hardened under pressure, is now frozen. No particular limitations are set on the freezing conditions. Typically, the ceramic block is frozen in a freezer. After freezing, the ceramic material is released out of the core, and is fully dried prior to firing. To prevent the ceramic block from being quickly thawed during a release operation, a lower freezing temperature is desirable. For this reason, the ceramic material may be frozen in a low-temperature freezer or may be immersed in a cryogenic temperature liquid such as a liquid nitrogen when a even lower temperature is required. According to the present invention, a frozen ceramic block is obtained prior to firing, machined by a carbide bar for shaping, smoothed by a soft brush, and then adjusted by a cotton puff. In this way, a high precision artificial tooth is fired.

Since the ceramic material shrinks in the firing process, the shrunk portion has to be compensated for to obtain an artificial tooth as defined by the impression. The compensation is typically performed by molding or additional injection of the cream into the core. The direction of injection and the location of the injection port need attention. The ceramic cream runs down, and there is no problem if an additional injection of cream through the initial injection port reaches the interior of the core as shown in FIG. 1. FIG. 1 shows a core 1, an artificial tooth 2 and an injection port 3. Referring to FIG. 2, a first injection is performed from the side of a metal frame 4. When an additional injection is made from the same side, a cavity A where ceramic cream is unable to reach is inevitably caused. Such an injection results in a poor product. To avoid such a problem, an injection port 5 dedicated to an additional injection is formed in this embodiment. The injection port 5 is formed at the same time as the core 1. Another core 6 (as represented by a cross-hatched structure) matching the injection port 5 is formed. The core 6 is mated into the core 1 to be a unitary body for the first injection. The core 6 is then pulled out of the core 1 for the additional injection for compensation, the injection port 5 is exposed with the entire core placed upside down, and the additional ceramic cream is then injected. In this way, the ceramic cream sufficiently fills the cavity A. Alternatively, the injection port 5 may be formed by machining the core 1 immediately prior to the second injection if the core 1 is easy to machine. The core is partitioned into two parts in this embodiment. To achieve a proper direction of pressurization, the core may be partitioned into three or more parts. Since the surface of the ceramic material after firing is extremely smooth according to the present invention, there is a possibility that no sufficiently strong bond is achieved between the fired ceramic material and the additional ceramic cream. The surface of the fired ceramic material is sandblasted as necessary to positively cause surface roughness.

According to the present invention, the cream of ceramic powder is poured into the core for the artificial tooth, the ceramic cream is compacted and hardened by applying pressure, water oozed out under pressure is removed, the resulting ceramic block is frozen, and the frozen ceramic block is released out of the core subsequent to the freezing. A high-precision structured ceramic block is thus obtained. The ceramic material is frozen with most of moisture removed. The ceramic block, thawed and dried, is compact in structure rather than porous, and thus a high-precision artificial tooth thus results.

Instead of removing water, ceramic powder is additionally fed to be mixed in water. This method heightens the packing to the core, reducing an additional injection quantity subsequent to firing and shrinkage. As specified in a third aspect of the present invention, the pressurization process is repeated for several times, the density of the ceramic block is made even higher, and a high-precision artificial tooth is accordingly obtained.

The ceramic block, released out of the core subsequent to freezing, may be subjected to a secondary machining prior to firing. More particularly, the ceramic block with its frozen state kept is ground by a disk or point bar driven by an engine, ground using a knife or a brush. By applying a paste opaque on the surface, an opaque layer is easily formed, and the opaque layer and the ceramic block are simultaneously fired. Such a process cannot be performed using the conventional artificial tooth technique. In additional process, it is necessary to preclude a crack or a peel taking place on the additional portion. When the mixing liquid is water only, a peeling resulting from the different thermal expansion coefficients between the ceramic material surface and the frozen block occasionally takes place. Cracks and peeling at the thawing were substantially reduced by the addition of a medium, such as ethanol, having hydrophilic nature and being a liquid, when added, and completely combusted at the firing process. Adding a medium of this type to the mixing liquid as necessary is effective. A freeze-resistant liquid such as a mixing liquid of paste opaque may be used to add the ceramic cream to the surface of the frozen ceramic block.

What is claimed is:

1. A manufacturing method of an artificial tooth comprising the steps of pouring a cream of ceramic powder, wherein said ceramic powder has a substantially uniform particle diameter, into a flexible core, compacting and hardening the ceramic cream, removing water oozed out of the ceramic cream by pressure, freezing the flexible core with the ceramic cream loaded therein, releasing the frozen block of the ceramic cream out of the flexible core subsequent to the freezing step, thawing the frozen ceramic block, drying the ceramic block, and firing the ceramic block in a furnace.

2. A manufacturing method of an artificial tooth according to claim 1, wherein the ceramic powder has a substantially uniform particle diameter of 50 µm or smaller.

3. A manufacturing method of an artificial tooth comprising the steps of pouring a cream of ceramic powder into a core, applying pressure to the ceramic cream to compact and harden the ceramic cream, removing water oozed out under pressure, freezing the core with the ceramic cream loaded therewithin, releasing the block of the frozen ceramic cream out of the core subsequent to the freezing step, thawing the ceramic block, drying the ceramic block, and firing the ceramic block in a furnace.

4. A manufacturing method of an artificial tooth comprising the steps of pouring a cream of ceramic powder into a core, applying pressure to the ceramic cream to compact and harden the ceramic cream, adding additional ceramic powder to water oozed out under pressure to form additional cream of ceramic powder and adding into the core and pressing, thereby increasing packing to the core and minimizing the amount of material which must be subsequently added to compensate for shrinkage, freezing the core with the ceramic cream loaded therewithin, releasing the block of the frozen ceramic cream out of the core subsequent to the freezing step, thawing the ceramic block, drying the ceramic block, and firing the ceramic block in a furnace.

5. A manufacturing method of an artificial tooth according to claim 4, wherein the ceramic block released out of the core subsequent to the freezing step is reshaped by molding with separately prepared cream or ceramic powder.

6. A manufacturing method of an artificial tooth according to claim 4, wherein the ceramic block released out of the core subsequent to the freezing step is reshaped by applying an opaque material.

7. A manufacturing method of an artificial tooth according to claim 4, wherein a pressure vessel is used to apply pressure.

8. A manufacturing method of an artificial tooth according to claim 4, wherein a press is used to apply pressure.

9. A manufacturing method of an artificial tooth according to claim 3, wherein the ceramic block released out of the core subsequent to the freezing step is reshaped by grinding.

10. A manufacturing method of an artificial tooth according to claim 3, wherein the ceramic block released out of the core subsequent to the freezing step is reshaped by molding with separately prepared cream or ceramic powder.

11. A manufacturing method of an artificial tooth according to claim 3, wherein the ceramic block released out of the core subsequent to the freezing step is reshaped by applying an opaque material.

12. A manufacturing method of an artificial tooth according to claim 3, wherein a pressure vessel is used to apply pressure.

13. A manufacturing method of an artificial tooth according to claim 3, wherein a press is used to apply pressure.

14. A manufacturing method of an artificial tooth according to claim 7, wherein said pressure vessel applies a pressure of up to about 7 kg/cm$^2$.

15. A manufacturing method of an artificial tooth according to claim 12, wherein said pressure vessel applies a pressure of up to about 7 kg/cm$^2$.

* * * * *